United States Patent [19]

Kurozumi et al.

[11] Patent Number: 4,788,700

[45] Date of Patent: Nov. 29, 1988

[54] FLUORESCENT X-RAY ANALYZING METHOD OF SOLUTION SPECIMEN AND SPECIMEN SAMPLER USED FOR THE METHOD

[75] Inventors: Shigetoshi Kurozumi, Settsu; Tadahiro Abe, Chiba; Hideo Maruyama, Mukou; Noriko Yasui, Yachiyo, all of Japan

[73] Assignees: Rigaku Industrial Corporation, Takatsuki; Kawaski Steel Corporation, Kobe, both of Japan

[21] Appl. No.: 928,657

[22] Filed: Nov. 5, 1986

Related U.S. Application Data

[63] Continuation of Ser. No. 645,795, Aug. 30, 1984, abandoned.

[51] Int. Cl.$^4$ .................. G01N 23/223; H05G 1/00
[52] U.S. Cl. .................................. 378/44; 378/45; 378/208
[58] Field of Search ................ 378/44, 45, 86, 88, 378/208, 53, 68, 79, 47; 436/165, 169, 172; 250/304

[56] References Cited

U.S. PATENT DOCUMENTS

| | | |
|---|---|---|
| 3,624,394 | 11/1971 | Youngman et al. |
| 4,059,405 | 11/1977 | Sodickson et al. ............... 436/172 |
| 4,080,171 | 3/1978 | Sano et al. ....................... 378/45 |
| 4,587,666 | 5/1986 | Torrisi et al. .................... 378/208 |
| 4,643,033 | 2/1987 | Solazzi ............................ 378/208 |
| 4,698,210 | 10/1987 | Solazzi ............................ 378/45 |

FOREIGN PATENT DOCUMENTS 1798423 12/1967 Fed. Rep. of Germany.
56-61637 5/1981 Japan.

OTHER PUBLICATIONS

Ueki, Kunimasa, *Determination of Ores by X-ray Analysis (II)*, vol. 13(4), 1977, pp. 249–255.
Chemical Abstracts 88(24):181895f, 89(2):16216y, 102(4):39056x, dated 1977, 1977 and 1984 respectively.

*Primary Examiner*—Carolyn E. Fields
*Assistant Examiner*—Joseph A. Hynds
*Attorney, Agent, or Firm*—Spencer & Frank

[57] ABSTRACT

For analyzing the solution specimen according to the fluorescent X-ray analyzing method, a certain quantity of solution specimen to be analyzed is impregnated into a thin porous sheet, for example by dripping method, and the sheet is dried for evaporating the solvent. Held on an appropriate holder, for example, the sheet is placed in the vacuum atmosphere or the atmosphere of helium gas, so that the primary X-rays are irradiated and the wavelength or the intensity of the fluorescent X-rays generated from the solute remained in the sheet may be detected. The concentration of the solution may be changed by concentration or by dilution, so that an adequate intensity of the fluorescent X-ray may be generated. The specimen sampler is made of porous sheet material, to which the solution specimen to be analyzed is impregnated and dried to remain only the solute of the solution in the sheet. To the circumferential edge of the sheet is attached a circular edge of a support, so that the central portion of the porous sheet is sufficiently spaced from the circumferentially provided support.

19 Claims, 3 Drawing Sheets

FLUORESCENT X-RAY ANALYZING METHOD OF SOLUTION SPECIMEN AND SPECIMEN SAMPLER USED FOR THE METHOD

This application is a continuation of application Ser. No. 645,795, filed Aug. 30, 1984, now abandoned.

BACKGROUND OF INVENTION

The present invention relates to a fluorescent X-ray analyzing method for solution specimens and a specimen sampler used for the method.

For the fluorescent X-ray analysis of a solution specimen, such as a plating liquid for steel plate, analysis has conventionally been made as follows: The liquid specimen is filled in a receptacle and the liquid surface is covered with a film of synthetic resin, etc. The specimen is then placed in a vacuum atmosphere or an atmosphere of helium gas, and primary X-rays have been irradiated through the synthetic resin film. However, since the specimen is in the form of liquid, much care has had to be taken in handling the specimen put into the vacuum or gas atmosphere. Further, it has been very difficult to keep the thickness of the synthetic resin film even or to the keep the condition of the specimen surface constant. Furthermore, there may be many bubbles on the liquid surface. These result in an error of the analyzed value. Particularly, in the so-called ON LINE analysis of a plating liquid, etc., It is extremely difficult to analyze the solution specimen in a vacuum or helium gas atmosphere, and therefore the analysis has been made in the air. Therefore, ON LINE analysis of ligh chemical elements such as titanium of atomic number 22, or those with atomic numbers less than titanium, has actually been impossible. Any effective correction for light chemical elements has thus not been possible, and so this affects the precision of analysis for the major component made of a heaver chemical element. The analysis of the entire composition has thus not been possible, and for this reason, the mixing of chemicals, for example, has becomes difficult.

In the meantime, a method for analyzing a solution specimen using a sheet-type, porous material, such as filter paper, has become known. According to this method, the solution specimen is first impregnated into the porous sheet material, is dried, and analyzed by a fluorescent X-ray analyzing machine. By this method, a precise analysis may be made with relatively ease. However, in such conventional porous sheets used as the specimen samplers, thin porous sheet material is used, and so it is likely to bend, and its mechanical strength is weak. For this reason, it has been a hard task to mount a specimen sampler in a desired position in the machine without injuring or breaking it. During the already-mentioned drying operation, the sheet might be bent easily. Thus it has been not easy to handle the sheet. For these reasons, it has been difficult heretofore to prepare an automatic machine for impregnating solution into the sheet, drying and mounting and demounting the sheet to and from the machine.

It is a primary object of this invention to provide a method for analyzing solution specimens, which can precisely analyze a small quantity of the solution specimen.

It is another object of this invention to provide specimen samplers made of porous sheet material, which can overcome the drawbacks of the conventional samplers.

SUMMARY OF INVENTION

According to the method of the present invention, a predetermined quantity of solution specimen to be analyzed is impregnated into a thin porous sheet, for example by dripping, and the sheet is dired to evaporate the solvent. Held on an appropriate holder, for example, the sheet is placed in a vacuum atmosphere or an atmosphere of helium gas, so that primary X-rays are irradiated thereon and the wavelength or the intensity of the fluorescent X-rays generated from the solute remaining in the sheet may be detected. In this case, the concentration of the solution may be changed by concentration or by dilution, so that an adequate intensity of the fluorescent X-ray may be generated.

The specimen sampler according to the present invention is made of porous sheet material, onto to which the solution specimen to be analyzed is impregnated and dried so that only the solute of the solution remains in the sheet. To the circumferential edge of the sheet is attached the circular edge of a support, so that the central portion of the porous sheet is sufficiently spaced from the circumferentially provided support.

DESCRIPTION OF EMBODIMENTS

Figure 1:
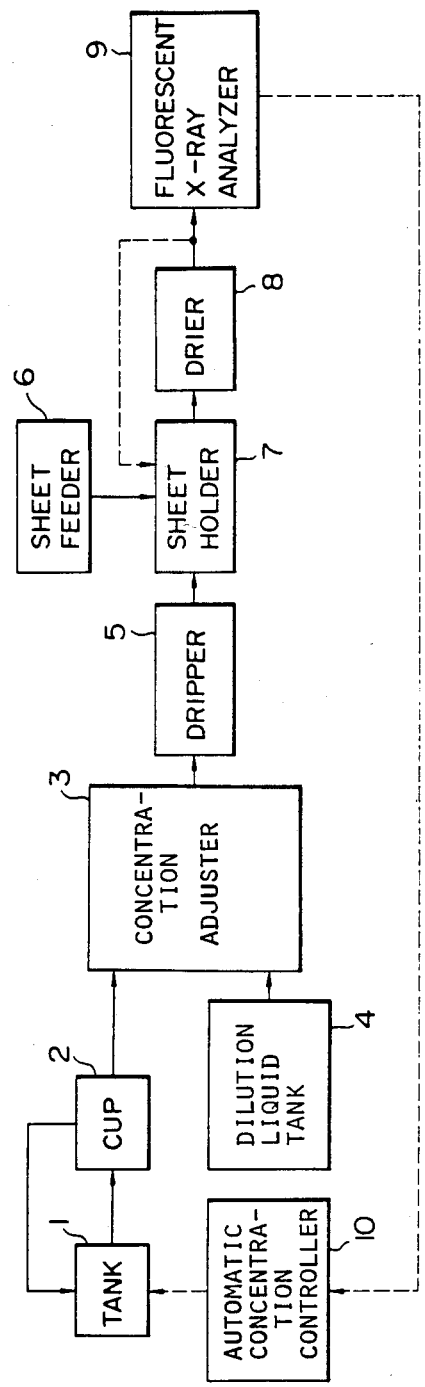
FIG. 1 is a block diagram showing the process of an embodiment of the fluorescent X-ray analyzing method according to this invention.

FIG. 1 is a block diagram showing an embodiment of the process for the fluorescent X-ray analyzing method according to the present invention. Specimen is dissolved in adequate solvent to obtain the solution specimen, which is filled into a tank 1. The solution specimen is poured into a specimen cup 2, and the amount exceeding a predetermined scale line of the cup 2 is returned to the tank 1, to obtain a predetermined amount of specimen solution to be poured into a density or concentration adjuster 3. In a dilution liquid tank 4, solvent of the type mentioned above is filled, so that desired amount of solvent may be added to the adjuster 3 and stirred to obtain the desired diluted solution. Or, alternatively, the solution poured from the cup 2 into the adjuster 3 may be heated within the concentration adjuster 3 so as to evaporate solvent to obtain a predetermined concentration of the solution. Thus, a solution specimen of desired percentage of solution obtained by concentration or dilution is moved from the adjuster 3 into a dripper 5, to drip the solution onto a porous sheet, such as a filter paper, fed one by one from a sheet feeder 6 onto a sheet holder 7. The sheet with the dripped solution specimen therein is further fed to a drier 8, where it is dried. At this stage, the solvent is evaporated, and therefore only solute, which had been dissolved in a predetermined amount of solution, remains on and in the sheet. The sheet is then further fed to a fluorescent X-ray analyzing device 9, where the sheet is placed in vacuum or gas atmosphere and, the primary X-rays are irradiated, therein and the fluorescent X-rays from the solute in the sheet detected, the sheet at this stage not bearing any solvent, which is easily evaporated. In a so-called ON LINE system, there is a need to automatically adjust the concentration of the plating fluid, etc. according to the result of the fluorescent X-ray analysis, and an automatic concentration controller 10 may be provided in order to automatically adjust the solution concentration of the tank 1. By inputting an output signal from the analyzing device 9 into this automatic controller 10, necessary addition of some chemicals into the tank 1 according to the result of the analysis may be possible. Thus the composition of the plating liquid may automatically be controlled. The adjusted plating liquid thus may be supplied into a plating liquid bath, not shown. If desired, the heating mechanism of the solution attached to the concentration adjuster 3 may be dispensed with. In place thereof, the sheet after being dried by the drier 8 is fed back to the holder 7, as shown by a dotted line in FIG. 1, repeatedly. By repeating the feedback, dripping by the dripper 5, and drying by the drier 8, the desired concentration of the solution may be obtained.

Figure 2:
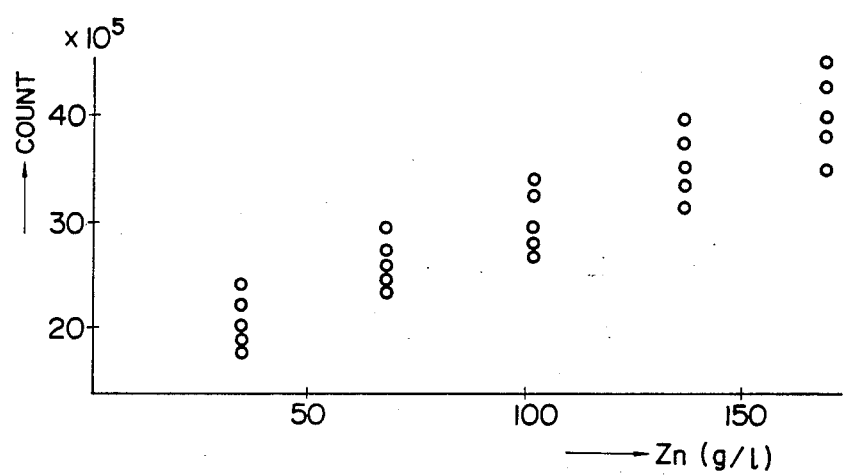
FIG. 2 is a graph showing the result of analysis by a conventional solution specimen analyzing method.
Figure 3:
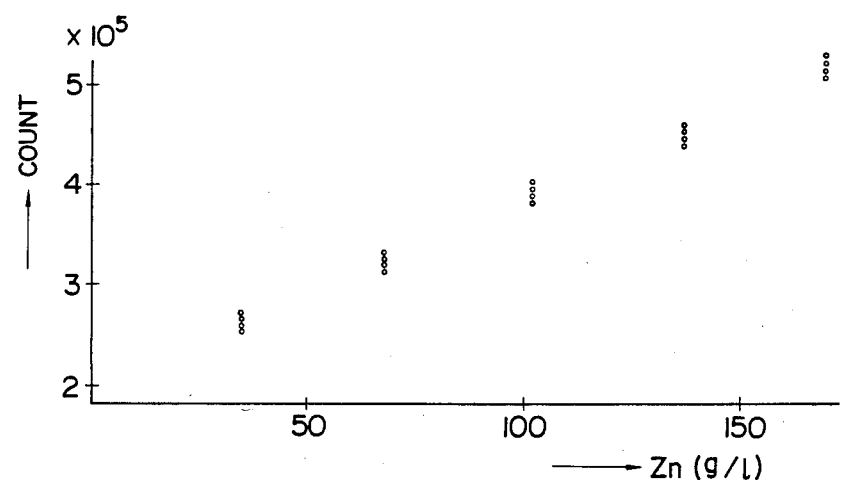
FIG. 3 is a graph showing the result of analysis by an embodiment of the method of this invention.

In the example of FIG. 2, the specimen used is the plating liquid for plating Zn-Ni alloy onto a metal plate. The characteristic X-ray of the zinc included in the specimen liquid is measured. In the graph of FIG. 2, the amount (g) of zinc in a solution of one liter (l) is given on the X-coordinate, while the count of the characteristic X-ray is given on the Y-coordinate. In ordinary cases, in the plating liquid for Zn-Ni alloy has, sulfate ions ($SO^{-4}$) of Na, Fe, etc. other than SAn and Ni added, and the concentration thereof relative to the plating liquid changes from time to time. Therefore, although the amount of element to be analyzed is constant, the fluorescent X-ray intensity of the element to be analyzed varies much according to the influence of concomitants. FIG. 2 shows the above-mentioned, fact for the measured resuilts of five specimens with different amounts of concomitants, when the amount of Zn is 35, 68, 101, 136 and 169 g/l, respectively. As will be seen from the graph, the measured results are much affected by the concomitants included in the solution specimens. Even by any ordinary correction of the results, much precision in the results will not be expected. On the other hand, FIG. 3 shows the results according to the present invention using the solution specimen diluted to 20 times as thin as the specimens of FIG. 2, respectively, each of which is dripped on the porous sheet of filter paper and then dried. According to this method, as will be seen from the graph of FIG. 3, the influence of concomitants may much be lessened. Thus, the error between the measured values becomes small, enabling a precise analysis, which will further be improved by adequate correction.

As described above, according to the method of the present invention, solution specimen is impregnated into a porous sheet and the solvent is removed by drying the sheet. Therefore, the sheet may be placed in a vacuum or gas atmosphere and the analysis may be made without any difficulty. Thus, the influence by the solvent and the film of synthetic resin covering the liquid surface according to the prior art is avoided. Even specimens consisting of the lighter elements may be analyzed with considerable precision. Further, handling of the specimen in the analyzing device becomes very easy. The influence of concomitants may be avoided, since the solution specimen may be diluted or concentrated as desired. Analysis of micro-amounts of elements may also be made by providing an adequate numbers of count. Thus, the analysis precision is improved and also the extent of application is made very wide. It should be realized that, for the analysis, only a small quantity of solution specimen suffices.

Figure 4:
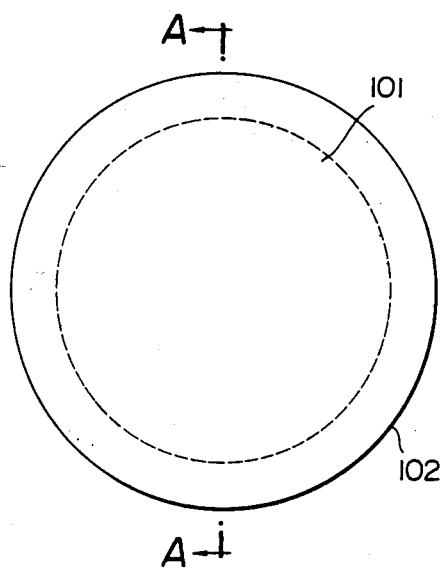
FIG. 4 is a front view of a first embodiment of the specimen sampler according to the present invention.
Figure 5:
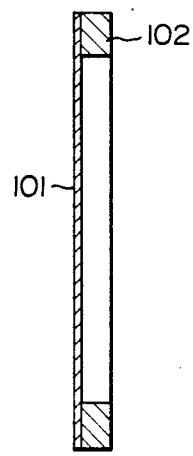
FIG. 5 is an A—A section of FIG. 4.

Now an explanation will be given for the first embodiment of a specimen sampler of this invention, by referring to FIGS. 4 and 5. FIG. 4 is a front view of a first embodiment of sampler of this invention and FIG. 5 is the A—A sectional view of FIG. 4. The sampler in this embodiment is made of a circular sheet 101 whose diameter is several millimeters and thickness is several hundred micron meters. To the circumferential edge of the sheet 101, a ringshaped flat support 102 made of synthetic resin or metal sheet is attached with adequate adhering agent. The sheet 101 used is the same as commercially marketed filter papers usually used for filtrating to remove any precipitating or foreign substances from chemical experiments, etc. The sheet 101 is made of paper much softer than ordinary paper and of pure cellulose, etc., so that the sheet 101 can be impregnated to hold much water. It is desirable that the sheet 101 does not contain any elements other than carbon, hydrogen and oxygen.

Figure 6:
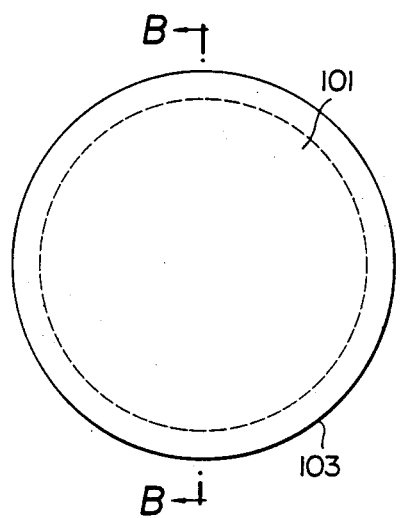
FIG. 6 is a front view of a second embodiment of the specimen sampler according to the present invention.
Figure 7:
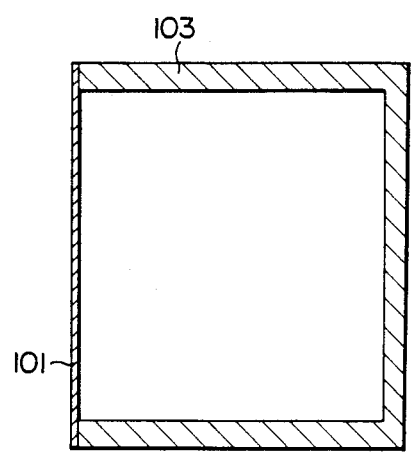
FIG. 7 is a B—B section of FIG. 6.

FIGS. 6 and 7 show a second embodiment of the specimen sampler according to this invention, FIG. 6 being the front view thereof and the FIG. 7 being the B—B sectional view of FIG. 6. Like the sampler shown in FIGS. 4 and 5, a porous sheet 101 in a circular form is used. In this case, the circumferential edge of the sheet 101 is attached to a hollow support 103 in the form of a cylindrical body having a base.

The specimen samplers as described with reference to FIGS. 4 through 7 may be used in the method of this invention already explained with reference to FIG. 1 through 3.

The support 102 or 103 enables the effective support of sheet 101, which is very soft and breaks easily. Thus, when the porous sheet is dried after the solution specimen is dripped, thereon any distortion or bending of the sheet 101 may be avoided by providing support 102 or 103. The sheet may thus be kept in the complete form of a plane. Measuring error from the change of incidence of the X-rays may be avoided. By the provision of the support 102 or 103, a sampler may be supported, moved or held in a desired state very easily, when dripping, drying, or mounting or demounting to or from the fluorescent X-ray analyzing device is done. Therefore, an automatic mounting and demounting machine for the sampler may be fabricated with ease. Since supports 102 or 103 are attached only to the circumferential edge of sheet 101, the back central portion of sheet 101 is spaced from the circumferential support, thus any error of detection from the incidence or scattering of primary X-rays an the support may be avoided.

Although the embodiment of the samplers has been explained as that in the cicular shaped sheet 101, it should be understood that any other form may be taken as desired.

What is claimed is:

1. An on-line, fluorescent X-ray analysis method comprising:
    supporting a porous sheet having a peripheral edge portion and a central portion on a sheet holder means so that only the peripheral edge portion of the porous sheet contacts the sheet holder means to provide a supported porous sheet;

impregnating the supported porous sheet by dripping onto the central portion thereof a measured amount of an on-line specimen solution to provide an impregnated sheet, which on-line specimen solution is a manufacturing process fluid comprises of a solvent and a specimen solute to be analyzed dissolved in said solvent;

drying the impregnated sheet to remove substantially all of the solvent therefrom and provide a dried sheet;

positioning the dried sheet in a chamber and surrounding same with a predetermined atmospheric environment to provide a positioned sheet;

irradiating the positioned sheet with primary X-rays to generate fluorescent X-rays from the specimen solute; and detecting one of wavelength and intensity of the fluorescent X-rays from the specimen solute as an output signal from a fluorescent X-ray analyzer.

2. The method according to claim 1, wherein the impregnating and drying steps are repeated until the amount of specimen solute impregnated in the positioned sheet provides a predetermined output signal from the fluorescent x-ray analyzer.

3. The method according to claim 1, wherein the peripheral edge portion of the porous sheet is attached to the sheet holder means by an adhering agent, such that the porous sheet is held substantially in one plane.

4. The method according to claim 3, wherein the porous sheet is a circular sheet having a peripheral edge portion and the sheet holder means includes a ring-shaped flat sheet, wherein the peripheral edge portion of the porous sheet is attached to one side of said ring-shaped flat sheet.

5. The method according to claim 3, wherein the porous sheet is a circular sheet having a peripheral edge portion and the sheet holder means includes a hollow cylindrical body having first and second ends, and a solid base member attached to said first end of the hollow cylindrical body, wherein the peripheral edge portion of the porous sheet is attached to said second end of the hollow cylindrical body.

6. The method according to claim 1, wherein the porous sheet consists of pure cellulose and contains no elements other than carbon, hydrogen and oxygen.

7. The method according to claim 1, wherein the predetermined atmospheric environment surrounding the positioned sheet is an evacuated environment.

8. The method according to claim 1, wherein the predetermined atmospheric environment surrounding the positioned sheet is a helium environment.

9. The method according to claim 1, wherein the porous sheet is supported substantially in one plane on the sheet holder means.

10. The method according to claim 1, wherein the impregnated sheet is substantially uniformly impregnated with the on-line specimen solution at least in the central portion thereof.

11. An automated, on-line fluorescent X-ray analysis method comprising:

measuring a predetermined, constant amount of specimen solution to provide a measured specimen solution, which measured specimen solution is a manufacturing process fluid comprised of a solvent and a specimen solute to be analyzed dissolved in said solvent;

measuring density of the measured specimen solution and subjecting the measured specimen solution to dilution when the density thereof exceeds a predetermined density, which predetermined density corresponds to a predetermined specimen solution concentration, and subjecting the measured specimen solution to evaporation when the density thereof is below the predetermined density, such that concentrationadjusted specimen solution is provided;

supporting a porous sheet having a peripheral edge portion and a central portion on a sheet holder means so that only the peripheral edge portion of the porous sheet contacts the sheet holder means to provide a supported porous sheet;

impregnating the supported porous sheet by dripping onto the central portion thereof the concentration adjusted specimen solution to provide an impregnated sheet;

drying the impregnated sheet to remove substantially all of the solvent therefrom and to provide a dried sheet;

positioning the dried sheet in a chamber and surrounding same with a predetermined atmospheric environment to provide a positioned sheet;

irradiating the positioned sheet with primary X-rays to generate fluorescent X-rays from the specimen solute; and detecting one of wavelength and intensity of the fluorescent X-rays from the specimen solute as an output signal from a fluorescent X-ray analyzer.

12. The method according to claim 11, wherein the porous sheet is supported substantially in one plane on the sheet holder means.

13. The method according to claim 11, wherein the impregnated sheet is substantially uniformly impregnated with the concentration adjusted specimen solution at least in the central portion thereof.

14. An automated, on-line, fluorescent X-ray analysis method, wherein the method is for on-line analysis and for automatic adjustment of on-line concentration of a specimen solution, which specimen solution is a manufacturing process fluid comprised of a solvent and a specimen solute to be analyzed dissolved in said solvent, the method comprising:

providing a storage tank for containing the specimen solution and filling the specimen solution into the storage tank;

supporting a porous sheet having a peripheral edge portion and a central portion on a sheet holder means so that only the peripheral edge portion of the porous sheet contacts the sheet holder means to provide a supported porous sheet;

removing a predetermined, constant amount of the specimen solution from the storage tank and impregnating the supported porous sheet by dripping onto the central portion thereof the specimen solution to provide an impregnated sheet;

drying the impregnated sheet to remove substantially all of the solvent therefrom and provide a dried sheet;

positioning the dried sheet in a chamber and surrounding same with a predetermined atmospheric environment to provide a positioned sheet;

irradiating the positioned sheet with primary X-rays to generate fluorescent X-rays from the specimen solute;

detecting one of wavelength and intensity of the fluorescent X-rays from the specimen solute as an output signal from a fluorescent X-ray analyzer;

ajdusting the concentration of the specimen solution remaining in the tank after the removal of the predetermined, constant amount of the specimen solution therefrom in response to the output signal from the fluorescent X-ray analyzer for the specimen solution by adding specimen solute to the specimen solution in the storage tank when the output signal is below a predetermined output signal, which predetermined output signal corresponds to a predetermined specimen solution concentration; and repeating the supporting, removing, impregnating, drying, positioning, irradiating, detecting, and adjusting steps, such that the on-line concentration of the specimen solution is automatically adjusted and maintained at a predetermined level to provide an adjusted specimen solution, and such that the adjusted specimen solution is supplied on-line to the manufacturing process which utilizes same.

15. The method according to claim 14, wherein the porous sheet is supported substantially in one plane on the sheet holder means.

16. The method according to claim 14, wherein the impregnated sheet is substantially uniformly impregnated with the specimen solution at least in the central portion thereof.

17. A specimen sampler to be used in, an automated, on-line, fluorescent x-ray analyzer, the specimen sampler comprising:

a porous sheet having a peripheral edge portion and a central portion; and sheet holder means attached by an adhering agent only to the peripheral edge portion of the porous sheet such that the central portion of the porous sheet is spaced from the edge holder means and the porous sheet is held substantially in one plane, said sheet holder means comprising means for holding a sample for x-ray fluorescent x-ray analysis.

18. The specimen sampler according to claim 17, wherein the porous sheet is a circular sheet and the sheet holder means includes a ring-shaped flat sheet, wherein the peripheral edge portion of the porous sheet is attached to one side of said ring-shaped flat sheet.

19. The specimen sampler according to claim 17, wherein the porous sheet is a circular sheet and the sheet holder means includes a hollow cylindrical body having first and second ends, and a solid base member attached to said first end of the hollow cylindrical body, wherein the peripheral edge portion of the porous sheet is attached to said second end of the hollow cylindrical body.

* * * * *